United States Patent [19]

Ryan et al.

[11] Patent Number: 4,698,355
[45] Date of Patent: * Oct. 6, 1987

[54] ANTI-HYPERTENSIVE AGENTS

[75] Inventors: James W. Ryan; Alfred Chung, both of Miami, Fla.

[73] Assignee: University of Miami, Coral Gables, Fla.

[*] Notice: The portion of the term of this patent subsequent to Sep. 1, 2004 has been disclaimed.

[21] Appl. No.: 64,903

[22] Filed: Aug. 14, 1979

[51] Int. Cl.$^4$ ............... A61K 31/40; A61K 31/41; C07D 207/00; C07D 211/72
[52] U.S. Cl. .................. 514/362; 514/363; 514/255; 514/308; 514/423; 548/531; 548/535; 546/310
[58] Field of Search .................. 424/177, 301; 260/112.5; 548/531, 535; 546/310; 514/255, 308, 423, 362, 363

[56] References Cited

U.S. PATENT DOCUMENTS

| | | | |
|---|---|---|---|
| 3,832,337 | 8/1974 | Ondetti | 260/112.5 |
| 3,891,616 | 6/1975 | Ondetti | 260/112.5 |
| 3,947,575 | 3/1976 | Ondetti | 424/177 |
| 4,046,889 | 9/1977 | Ondetti | 424/319 X |
| 4,052,511 | 10/1977 | Cushman | 424/274 |
| 4,053,651 | 10/1977 | Ondetti | 424/319 X |
| 4,070,361 | 1/1978 | Petrillo | 260/293.85 |
| 4,091,024 | 5/1978 | Ondetti | 260/293.85 |
| 4,105,776 | 8/1978 | Ondetti | 424/274 |
| 4,105,789 | 8/1978 | Ondetti | 424/309 |
| 4,108,886 | 8/1978 | Ondetti | 260/455 R |
| 4,113,715 | 9/1978 | Ondetti | 424/274 |
| 4,116,962 | 9/1978 | Ondetti | 260/293.63 |
| 4,129,566 | 12/1978 | Ondetti | 546/326 |
| 4,146,611 | 3/1979 | Ondetti | 424/177 |
| 4,151,172 | 4/1979 | Ondetti | 260/326.2 |
| 4,154,840 | 5/1979 | Ondetti | 424/267 |
| 4,154,934 | 5/1979 | Bernstein | 546/189 |
| 4,154,935 | 5/1979 | Ondetti | 546/189 |
| 4,154,937 | 5/1979 | Cushman | 546/221 |
| 4,168,267 | 9/1979 | Petrillo | 260/326.2 |

OTHER PUBLICATIONS

Cushman et al., Biochemistry, vol. 16, 1977, p. 5484.
Cushman et al., Experientia, vol. 29, 1973, p. 1032.
Ondetti et al., Science, vol. 196, 1977, p. 441.
Dorer et al., Biochem. Biophys. Acta, vol. 429, 1976, p. 220.
Fisher et al., Arch. Biochem. Biophys., vol. 189, 1978, p. 81.
Gavras et al., N. E. J. Med., vol. 291, 1974, p. 817.
Gavras et al., N. E. J. Med., vol. 298, 1978, p. 991.
Lipmann, Accounts Chem. Res., vol. 6, 1973, p. 6.
Lehninger, Biochemistry, Worth Pub., N.Y., 1970, pp. 153–157.
Ryan et al., Tissue & Cell, vol. 10, 1978, p. 555.
Cronyn et al., J. Am. Chem. Soc. 74, 4726 (1952).
Fischer et al., Ber. vol. 33 (1900).
Fisher, FEBS Letters, vol. 107 (1979).
Lehninger, A., Biochemistry, Worth Publications, Inc., New York (1975), pp. 189–195.
Ryan, J. W. et al., Biochem J 167, 501 (1977).
Methoden der Organischen Chem, (Houben–Weyl), vol. XV, Part I, p. 376 et seq. (1974).
Methoden der Organischen Chem. (Houben–Weyl), vol. XV, part II, p. 1 et seq. (1974).
Carter et al., J. Biol. Chem. 138, 627 (1941).
Engel et al., Proc. Soc. Exp. Biol. Med. 143, 483 (1973).
Klosterman et al., Biochem 6, 170 (1967).
Lijinski et al., Tetrahedron 26, 5137 (1970).
Nagasawa et al., J. Med. Chem. 16, 583 (1973).
Mita et al., Chem. Pharm. Bull. 26 (4), 1333–1335 (1978).
Kripalani et al., Clin. Pharmacol. Ther. 27 (5), 636–641, (1980).
Pfister et al., J Am. Chem. Soc. 71, 1096 (1949).
Merrifield, Adv. Enzymol 32, 221 (1969).
Ricci et al., Anal. Biochem. 79, 610 (1977).
Cushman, D. W. et al., Progr. Cardiovasc. Dis. 21, 176, 1978.
Oparil et al., Circ. Res. 32, 415 (1973).
Oparil et al., Circ. Res 29, 682 (1971).
Dorer et al., "Biochem J. 141, 915 (1974).
Sharpless, S. K., "Hypnotics and Sedatives", The Pharmacological Basis of Therapeutics, The Macmillan Co. (1965), pp. 105–128.
Kripalani, K. J. et al., Abstracts, Joint Meeting of AS-PET/SOT, Aug. 13–17, 1978.
Singhvi, S. M. et al., Abstracts, Joint Meeting of AS-PET/SOT, Aug. 13–17, 1978.
Wong, K. K. and Dreyfuss, J., Abstracts, Joint Meeting of ASPET/SOT, Aug. 13–17, 1978.
Buxton et al., J. Chem. Soc., p. 366 (1954).

Primary Examiner—Delbert R. Phillips

[57] ABSTRACT

Novel compounds are disclosed as potent inhibitors of angiotensin converting enzyme and as orally effective antihypertensive agents. The compounds have the general formula:

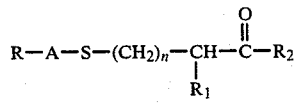

18 Claims, No Drawings

ANTI-HYPERTENSIVE AGENTS

BACKGROUND OF THE INVENTION

Angiotensin converting enzyme (peptidyldipeptide hydrolase, hereinafter referred to as ACE) occupies a central role in the physiology of hypertension. The enzyme is capable of converting the decapeptide angiotensin I, having the sequence AspArgValTyrIleHisProPheHisLeu to an octapeptide, angiotensin II by removal of the carboxy-terminal HisLeu. The symbols for various chemical entities are explained in the following table:

Ala=L-alanine
Arg=L-arginine
Asp=L-aspartic acid
<Glu=pyro-L-glutamic acid
Gly=glycine
Hip=Hippuric acid (Benzoyl glycine)
His=L-histidine
Ile=L-isoleucine
Leu=L-leucine
Phe=L-phenylalanine
ΔPro=L-proline
Pro=L-3,4-dehydroproline
Ser=L-serine
Trp=L-tryptophan
Tyr=L-tyrosine
Val=L-valine
ACE=Aniotensin converting enzyme Hepes=N-2-hydroxyethylpiperazine-N'-2-ethanesulfonic acid Angiotensin I is formed by the action of the enzyme renin, an endopeptidase found in kidney, other tissues and plasma, acting on a serum α-2 globulin.

Blood pressure is affected by certain peptides found in the blood. One of these, angiotensin II, is a powerful pressor (blood pressure elevating) agent. Another, bradykinin, a nonapeptide with the sequence ArgProProGlyPheSerProPheArg is a powerful depressor (blood pressure lowering) agent. In addition to a direct pressor effect, angiotensin II stimulates release of aldosterone which tends to elevate blood pressure by causing retention of extracellular salt and fluids. Angiotensin II is found in measurable amount in the blood of normal humans. However, it is found at elevated concentrations in the blood of patients with renal hypertension.

The level of ACE activity is ordinarily in excess, in both normal and hypertensive humans, of the amount needed to maintain observed levels of angiotensin II. However, it has been found that significant blood pressure lowering is achieved in hypertensive patients by treatment with ACE inhibitors. [Gavras, I., et al., *New Engl. J. Med.* 291, 817 (1974)].

ACE is a peptidyldipeptide hydrolase. It catalyzes the hydrolysis of the penultimate peptide bond at the C-terminal end of a variety of acylated tripeptides and larger polypeptides having an unblocked α-carboxyl group. The action of ACE results in hydrolytic cleavage of the penultimate peptide bond from the carboxyl-terminal end yielding as reaction products a dipeptide and a remnant.

The reactivity of the enzyme varies markedly depending on the substrate. At least one type of peptide bond, having the nitrogen supplied by proline, is not hydrolyzed at all. The apparent Michaelis constant (Km) varies from substrate to substrate over several orders of magnitude. For general discussion of the kinetic parameters of enzyme catalyzed reactions, see Lehninger, A., *Biochemistry*, Worth Publishers, Inc., New York, 1970, pp. 153–157. Many peptides which are called inhibitors of the enzymatic conversion of angiotensin I to angiotensin II are in fact substrates having a lower Km than angiotensin I. Such peptides are more properly termed competitive substrates. Examples of competitive substrates include bradykinin, and the peptide $BPP_{5a}$ (also called SQ20475) from snake venom, whose sequence is <GluLysTrpAlaPro.

Numerous synthetic peptide derivatives have been shown to be ACE inhibitors by Ondetti, et al. in U.S. Pat. No. 3,832,337 issued Aug. 27, 1974.

The role of ACE in the pathogenesis of hypertension has prompted a search for inhibitors of the enzyme that could act as antihypertensive drugs. See for example U.S. Pat. Nos. 3,891,616, 3,947,575, 4,052,511 and 4,053,651. A highly effective inhibitor, with high biological activity when orally administered, is D-3-mercapto-2-methylpropanoyl-L-proline, designated SQ14225, disclosed in U.S. Pat. No. 4,046,889 to Ondetti et al., issued Sept. 6, 1977, and in scientific articles by Cushman, D. W. et al., *Biochemistry* 16, 5484 (1977), and by Ondetti, M. et al., *Science* 196, 441 (1977). The inhibitor SQ14225 reportedly has an $I_{50}$ value of $2.3 \times 10^{-8}$ M. The $I_{50}$ value reported by Cushman, et al, supra is the concentration of inhibitor required to produce 50% inhibition of the enzyme under a standard assay system containing substrate at a level substantially above $K_m$. It will be understood that $I_{50}$ values are directly comparable when all potential factors affecting the reaction are kept constant. These factors include the source of enzyme, its purity, the substrate used and its concentration, and the composition of the assay buffer. All $I_{50}$ data reported herein have been performed with the same assay system and same enzyme (human urinary ACE) and with an approximately ½ $K_m$ level of substrate and are therefore internally consistent. Discrepancies with data obtained by other workers may be observed. Indeed such discrepancies do exist in the literature, for unknown reasons. See, for example, the $I_{50}$ values for $BPP_{9a}$ reported by Cushman, D. W., et al., *Experientia* 29, 1032 (1973) and by Dorer, F. E., et al., *Biochim. Biophys. Acta* 429, 220 (1976).

The mode of action of SQ 14,225 has been based upon a model of the active site of ACE developed by analogy with the better known related enzyme, carboxypeptidase A. The active site was postulated to have a cationic site for binding the carboxyl end group of the substrate and a pocket or cleft capable of binding the side chain of the C-terminal amino acid and providing especially tight binding for the heterocyclic ring of a terminal proline residue. A similar pocket for the penultimate amino acid residue was postulated, and the published data suggested a rather stringent steric requirement, since the D-form of the inhibitor was substantially more potent than its stereoisomer or the 3-methyl and unsubstituted analogs. The sulfhydryl group on the inhibitor, postulated to be bound at the active site near the catalytic center, was believed to play a central role in inactivation of the enzyme by combining with the zinc moiety known to be essential for catalytic activity. Substituents on the sulfhydryl, such as a methyl group, and an S-acetyl derivative, substantially reduced potency of the inhibitor. See Cushman, D. W., et al., *Biochemistry, supra.*

In vitro study of the mechanism by which SQ 14,225 and its analogs act to inhibit ACE has been somewhat hampered by the instability of these molecules under ambient conditions. For example, it has been observed that a fresh aqueous solution of concentration, e.g., 1 mg per ml of SQ 14,225 at a pH of about 8 becomes substantially less active upon standing for as little as 30 minutes, and that activity continues to decrease as the solution stands for longer periods. It is believed that this loss in activity is mainly the result of dimerization of SQ 14,225 occurring at the sulfhydryl end groups, whereby a disulfide is formed which is largely inactive as an inhibitor. Since the free sulfhydryl group is highly reactive and may be readily oxidized to polar acidic moieties such as sulfone and sulfoxide groups, it may also be that the observed in vitro loss of activity of aqueous solutions of SQ 14,225 on standing is in some part a consequence of one or more such oxidation reactions, with formation of a sulfone or sulfoxide which does not function effectively as an inhibitor for ACE.

Such reports of SQ 14,225 clinical testing as are currently available, some of which refer to the compound under the name "Captopril", suggest that the product is sufficiently stable in the normal gastric and intestinal environments of most patients to be an effective inhibitor for ACE when administered orally. It is not yet clear, however, whether there may be a group of patients for which SQ 14,225 is substantially ineffective. Because of the high reactivity of the free sulfhydryl group, SQ 14,225 could readily form mixed disulfides with serum, cellular proteins, peptides or other free sulfhydryl group-containing substances in the gastric or intestinal environments, in addition to the possibility for dimer formation or oxidative degradation reactions. A mixed disulfide with protein may be antigenic and, indeed, occasional allergic reactions have been clinically observed. See Gavras, et al., *New England J. Med.* 298, 991 (1978). Disulfides and oxidative degradation products of SQ 14,225, if formed, may at best be expected to be largely ineffective as inhibitors. It may be postulated accordingly that dose response to SQ 14,225 may vary with conditions of administration and among individual patients. Moreover, in at least some patients, unwanted side effects may occur and maintenance of an effective concentration of the inhibitor in the body may be difficult to control.

Thiolester compounds generally are thought to be highly reactive in that the thiolester linkage is readily hydrolyzable to a sulfhydryl moiety and a carboxylic moiety. Thiolesters are accordingly often used as active ester intermediates for acylation under mild conditions. Such groups as, e.g., acetylthio have been used as blocking groups in the above cited Ondetti, et al. patents. Thiolester intermediates are also postulated to occur in the biosynthesis of cyclic peptides such as tyrocidin or gramicidin S. See Lipmann, F. in *Accounts Chem. Res.* 6, 361 (1973).

Thiolester compounds having potent ACE inhibitory activity and oral effectiveness as anti-hypertensive agents have been disclosed in copending applications Ser. No. 116,950, filed Jan. 30, 1980, which is a continuation of Ser. No. 941,289, filed Sept. 11, 1978 (now abandoned in favor of its pending continuation Ser. No. 116,950, filed Jan. 30, 1980) and Ser. No. 958,180, filed Nov. 6, 1978 (abandoned in favor of its continuation Ser. No. 116,951, filed Jan. 30, 1980 which was abandoned in favor of its continuation, Ser. No. 295,589, filed Aug. 24, 1981 which was abandoned in favor of its continuation, Ser. No. 524,204, filed Aug. 18, 1983, which was abandoned in favor of its continuation, Ser. No. 680,541, filed Dec. 11, 1984, which was abandoned in favor of its pending continuation, Ser. No. 850,055, filed Apr. 10, 1986), both incorporated herein be reference. The previously disclosed compounds are: N-[3-(benzoylphenylalanylthio)-2-D-methylpropanoyl]-L-proline ($I_{50} \approx 1-4 \times 10^{-8}$ M), N-(2-benzoylphenylalanylthiopropanoyl)-L-proline ($I_{50} \approx 4-7 \times 10^{-8}$ M for racemic compound), N-(3-benzoylphenylalanylthiopropanoyl)-L-proline ($I_{50} \approx 7 \times 10^{-7}$ M), N-[3-(benzoylphenylalanylthio)-2-D-methylpropanoyl]-L-3,4-dehydroproline, N-(2-benzoylphenylalanylthiopropanoyl)-L-3,4-dehydroproline ($I_{50} = 3 \times 10^{-9}$ M for racemic compound), and N-(3-benzoylphenylalanylthiopropanoyl)-L-3,4-dehydroproline. Unless noted otherwise, all amino acids are in their L-forms.

Compounds related to SQ 14,225 have been disclosed by Ondetti, et al., U.S. Pat. Nos. 4,046,889, 4,052,511, 4,053,651, 4,113,715 and 4,154,840. Of interest are disclosed analogs of SQ 14,225 having the five-membered heterocyclic ring of proline replaced by a four- or a six-membered ring. The inhibitory potencies of such analogs relative to SQ 14,225 are not disclosed. Substitution of D-proline for L-proline is reported to drastically reduce inhibitory potency of 3-mercaptopropanoyl amino acids (Cushman, D. W., et al., supra).

SUMMARY OF THE INVENTION

Novel inhibitors of ACE are disclosed which have the general formula

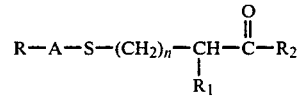

wherein,

R is L-arginyl, L-lysyl or L-pyroglutamyl;

A is L-phenylalanyl, glycyl, L-alanyl, L-tryptophyl, L-tyrosyl, L-isoleucyl, L-leucyl, L-histidyl, or L-valyl;

$R_1$ is hydrogen or methyl;

$R_2$ is L-proline, L-3,4-dehydroproline, D,L-3,4-dehydroproline, L-3-hydroxyproline, L-4-hydroxyproline or L-thiazolidine-4-carboxylic acid whose imino group is in imide linkage with the

and n is 0 or 1 such as when n=0, $R_1$ is methyl. The disclosed compounds are inhibitors of ACE and are useful as orally effective antihypertensive agents.

DETAILED DESCRIPTION OF THE INVENTION

The discovery of ACE inhibitory potency in the compounds of the present invention provides a unique approach to the design of inhibitory compounds. Although many prior art inhibitors are proline derivatives, substitution of other amino acids for proline has also yielded potent inhibitors. Arginine, phenylalanine and alanine are all effective substitutes for proline, so that a trend is not discernible.

The substitution of L-3,4-dehydroproline for proline has been studied in several systems. Substitution of L-3,4-ΔPro in the 7 position of bradykinin yields a bradykinin derivative which has significantly reduced physiological activity. See Fisher, G. H. et al., *Arch. Biochem. Biophys.* 189, 81 (1978). On the other hand, substitution of L-3,4-ΔPro at the 3,5 or 9 position in ACE inhibitor BPP$_{9a}$ enhances its inhibitory activity. In copending application Ser. No. 958,180 applicants found that the compounds having ΔPro, which are disclosed in said application, have high inhibitory potency and antihypertensive effectiveness. However, at present, no rationale can be advanced to explain the diversity of observed results following substitution of ΔPro for proline. Similarly, no clear picture has emerged of the effects of other proline derivatives or analogs substituted at various loci on ACE inhibitors.

To date, the effect of the amino acid to the left of the sulfur in the above-shown formula, has not been determined. It is thought that this amino acid functions as an additional recognition site for the enzyme. If this is true, it would be expected that a compound with an amino acid here would be a better inhibitor. It was not known which, if any, amino acids would be effective in this position and which if any would enhance the inhibitory activity of a given compound. Applicants have found that various amino acids are effective and that the hydroxyprolines, proline, L-, and D,L-,3,4-dehydroproline, and thiazolidine-4-carboxylic acid derivatives are all effective anti-hypertensive agents and have high inhibitory potency for ACE.

The present invention will be further described by the following examples. In these examples, the thin-layer chromatography (TLC) was performed using silica gel plates. The numerical solvent systems for use in the TLC procedures are as follows.

(1) is methanol:chloroform, 1:1 (parts by volume). (2) is benzene:water:acetic acid, 9:1:9 (parts by volume). (3) is acetic acid:water:n-butanol 26:24:150 (parts by volume). (4) is n-butanol:pyridine:acetic acid:water, 15:10:3:12 (parts by volume). (5) is chloroform:methanol:ammonium hydroxide, 60:45:20 (parts by volume). The buffers for paper electrophoresis were: pH 1.9—formic acid:acetic acid:water, 3:2:25 (parts by volume); pH 5.0—diethylene glycol:acetic acid:pyridine:water, 100:6:8.5:885 (parts by volume). The tert-butyloxycarbonyl derivatives of the amino acids are commercially available.

EXAMPLE 1

ACE activity assay. For most experiments described herein, the enzyme was assayed in 0.05 M Hepes buffer, pH 8.0 containing 0.1 M NaCl and 0.75 M Na$_2$SO$_4$. The substrate employed was Benzoyl-GlyHisLeu at a final concentration of $1 \times 10^{-4}$ M, ($K_m \approx 2 \times 10^{-4}$ M), together with about 130,000 cpm of [$^3$H]-Benzoyl-GlyHisLeu (25 Ci/mmole). Enzyme was diluted in the above buffer such that 40 μl buffered enzyme was capable of hydrolyzing 13% of substrate in a 15-minute incubation at 37° C. To initiate the assay, 40 μl of enzyme and 10 μl of water or inhibitor dissolved in water were preincubated ror five minutes at 37° C. Substrate, 50 μl, was then added to initiate reaction and the solution was incubated for 15 minutes at 37° C. To terminate the reaction, 1 ml of 0.1 M HCl was added, following which 1 ml of ethyl acetate was added. The mixture was agitated on a rotary mixer and centrifuged briefly to separate the phases.

An aliquot, 500 μl, of the ethyl acetate layer was transferred to a liquid scintillation vial containing 10 ml of Riafluor, trademark New England Nuclear Corporation, Boston, Mass. For determination of I$_{50}$ values, enzyme activity in the presence of inhibitor at a series of different concentrations was compared to activity in the absence of inhibitor. A plot of inhibitor concentration versus percent inhibition yielded the I$_{50}$ value.

EXAMPLE 2

Synthesis of 3-acetylthiopropanoyl-L-proline-t-butyl ester 3-acetylthiopropanoic acid, 0.865 g, was dissolved in 2 ml redistilled tetrahydrofuran (THF) and cooled to 0° C. A cooled solution of dicyclohexylcarbodiimide, 1.2031 g in 2 ml of THF was added, following which a cooled solution of L-proline-t-butyl ester, 1 g, was added. The reaction mixture was stirred at 0° C. for one hour, then at 4° C. overnight. The reaction mixture was then filtered and the precipitate was washed with ethyl acetate. Solvents of the filtrates were removed under reduced pressure in a rotary evaporator. The residue was dissolved in ethyl acetate which was then washed three times with cold 1 N citric acid, twice with saturated NaCl, twice with cold 1 N NaHCO$_3$ and three times with saturated NaCl. The solution was dried over anhydrous MgSO$_4$ and filtered. The solvent was removed under reduced pressure in a rotary evaporator at 30° C. yielding a clear colorless oily product in approximately 87% yield. The product migrated as a single spot in thin layer chromatography in five solvent systems.

EXAMPLE 3

Synthesis of 3-mercaptopropanoyl-L-proline

The product from Example 2, 3-acetylthiopropanoyl-L-proline-t-butyl ester, 0.5 g, was mixed with 4.5 ml of 5.5 N methanolic ammonia at room temperature under nitrogen for one hour to remove the acetyl group. The solvent was then removed at 25° C. with a rotary evaporator. After the product was taken up in methanol and reevaporated twice more in the rotary evaporator, the clear oily residue was dissolved in ethyl ether, washed twice with 5% potassium bisulphate and once with saturated NaCl, dried over MgSO$_4$ and filtered. Residual solvent was removed in vacuo to yield a clear oily product, migrating as a single spot on thin layer chromatography in three separate solvent systems. The t-butyl ester protecting group was removed by reaction with trifluoroacetic acid in anisole.

EXAMPLES 4-6

By substituting 2-acetylthiopropanoic acid, 3-acetylthio-2-D-methylpropanoic acid, or 3-acetylthio-2-D,L-methylpropanoic acid for the 3-acetylthiopropanoic acid in Example 2 and substantially following the procedures of Examples 2 and 3, the following compounds are obtained. By removing the t-butyl ester protecting group with trifluoroacetic acid in anisole as a first step, the dicyclohexylamine salt can be formed to assist in the resolution of isomers. The acetyl protecting group can be removed in a second step using methanolic ammonia, as described in Example 3.

| Example | Compound |
| --- | --- |
| 4 | 2-mercaptopropanoyl-L-proline |
| 5 | 3-mercapto-2-D-methylpropanoyl-L-proline |
| 6 | 3-mercapto-2-D,L-methylpropanoyl-L-proline |

EXAMPLE 7

Synthesis of
3-mercapto-2-methyl-propanoyl-L-3,4-dehydroproline

L-3,4-dehydroproline ($\Delta^3$Pro), 1 mmole, is dissolved in DMF and the solution is cooled to −15° C. The solution is neutralized by adding 1 equivalent of N-ethyl morpholine. In a separate reaction vessel at −10° C., one equivalent of 3-acetylthio-2-methyl-propanoic acid in an equal volume of DMF is mixed with 1.1 equivalent of 1,1′-carbonyldiimidazole, and the solution is stirred for one hour. The first solution containing $\Delta^3$Pro is mixed with the second, containing 3-acetylthio-2-methyl propanoic acid while maintaining the temperature at −10° C. The combined solution is stirred for 1 hour at −10° C. The solution is then allowed to warm slowly to room temperature. The solvent is removed on a rotary evaporator under reduced pressure at 40° C. Ethyl acetate (25 ml) is added and the solution is cooled to 0° C. Two ml of 1 N citric acid is added, the two phases are mixed and then allowed to separate. The phases are separated with a separating funnel, and the organic phase is washed twice more with 2 ml 1 N citric acid, two times with saturated NaCl and finally dried over anhydrous MgSO$_4$. The MgSO$_4$ is removed by filtration, and the solvent is removed with a rotary evaporator. The residue is dissolved and recrystallized from a non-polar solvent such as benzene to yield 3-acetylthio-2-D,L-methylpropanoyl-L-3,4-dehydroproline. When the 2-D-methyl isomer is desired, the residue is dissolved in acetonitrile (approximately 3 ml) and the solution is warmed to 40° C. One equivalent of dicyclohexylamine is added, and the solution is allowed to stand at room temperature overnight. The crystals are collected by filtration and are washed three times with acetonitrile. When further purification is required, the material can be recrystallized from isopropanol. The acetyl protecting group can be removed as in Example 3.

EXAMPLES 8–11

By substituting D,L-3,4-dehydroproline, L-3-hydroxyproline, L-4-hydroxyproline, or L-thiazolidine-4-carboxylic acid for the L-3,4-dehydroproline in Example 7 and substantially following the procedures of Example 7 the following compounds are obtained.

| Example | Compound |
| --- | --- |
| 8 | 3-mercapto-2-D-methylpropanoyl-D,L-3,4-dehydroproline |
| 9 | 3-mercapto-2-D-methylpropanoyl-L-3-hydroxyproline |
| 10 | 3-mercapto-2-D-methylpropanoyl-L-4-hydroxyproline |
| 11 | 3-mercapto-2-D-methylpropanoyl-L-thiazolidine-4-carboxylic acid |

EXAMPLE 12

Similarly, by substituting 3-acetylthiopropanoic acid or 2-acetylthiopropanoic acid for the 3-acetylthio-2-methyl propanoic acid of Examples 7–11, the L-3,4-dehydroproline, D,L-3,4-dehydroproline, L-3-hydroxyproline, L-4-hydroxyproline and L-thiazolidine-4-carboxylic acid derivatives are obtained, following substantially the described procedures.

EXAMPLE 13

Preparation of pyro-L-glutamyl-L-phenylalanine benzyl ester

A solution of 0.52 g of pyro-L-glutamic acid, 1.72 g of L-phenylalanine benzyl ester toluenesulfonic acid and 0.55 mg of N-ethylmorpholine in 5 ml of dimethylformamide (DMF) and 20 ml of dichloromethane was cooled in an ice bath with stirring. A solution of 0.826 g of dicyclohexylcarbodiimide in 2 ml dichloromethane was added to the above reaction mixture. The reaction mixture was stirred in an ice water bath for 1 hour and then at room temperature overnight. Dicyclohexylurea was removed by filtration and the product was washed in ethyl acetate. Solvents of the combined filtrates were removed under reduced pressure with a rotary evaporator at 40° C. Ethyl acetate (25 ml) was added to the residue and the organic solution was washed until neutral. The organic phase was dried over anhydrous MgSO$_4$, filtered and then the solvent was removed with a rotary evaporator. The material was crystalized from isopropanol and ether, yield: 1.01 g of white needles, m.p. 103°–104.5° C. The material was homogeneous on all TLC and electrophoresis systems.

Elemental analysis:

|   | Calculated | Found |
| --- | --- | --- |
| C | 68.84 | 68.58 |
| H | 6.05  | 6.05  |
| N | 7.64  | 7.56  |

EXAMPLE 14

Preparation of pyro-L-glutamyl-L-phenylalanine

The benzoyl ester protecting group of the compound of Example 13 (1.0 g) was removed by catalytic hydrogenolysis with 150 mg of 10% (by weight) Pd on carbon in 0.15 ml of glacial acetic acid and 15 ml of ethanol at 20 psi of H$_2$ at room temperature overnight. The catalyst was removed by filtration. Solvent was removed with a rotary evaporator. The material was crystalized from isopropanol and benzene, to yield a total of 402 mg of white crystals, m.p. 147°–149° C. The material was homogeneous on electrophoresis at pH 1.9 and pH 5.0 and on TLC in systems 1, 2 and 3.

Elemental analysis:

|   | Calculated | Found |
| --- | --- | --- |
| C | 60.86 | 60.37 |
| H | 5.84  | 5.85  |
| N | 10.14 | 9.98  |

EXAMPLE 15

Preparation of N$^\alpha$-[3-(Pyro-L-glutamyl-L-phenylalanylthio)-2-D-methylpropanoyl]-L-proline A solution of 87 mg of 1,1′-carbonyldiimidazole in 1.0 ml DMF was added to a solution of 139 mg of the product of Example 14 in 0.5 ml DMF at −15° C. The reaction mixture was stirred at −10° C. for 1 hour, and then a mixture of 119.5 mg of 3-mercapto-2-D-methylpropanoyl-L-proline and 0.072 ml of N-ethyl morpholine in 1 ml. DMF was added. The reaction mixture was stirred at −10° C. for an additional hour and then was slowly warmed to room temperature. DMF was removed under reduced pressure with a rotary evaporator at 40° C. and then 7 ml ethyl acetate and 2 ml 1 N citric acid were added. The organic phase was washed two times with 1 N citric acid and two times with saturated NaCl. The organic phase was dried with anhydrous MgSO$_4$ and then filtered. Solvent was removed using a rotary evaporator. The residue was purified on sephadex G-25[1] (1.2×99 cm) partition column chromatography with n-butanol: acetic acid: H$_2$O (4:1:5 by volume). The product was homogeneous on TLC (systems 1, 2 and 3) and on electrophoresis at pH 5.0.

Trademark, Pharmacia, Inc., Uppsala, Sweden.

EXAMPLE 16

By substituting N,$^\alpha$N$^\epsilon$-bis-t-butyloxycarbonyl-L-lysine (hereinafter bis-boc-L-Lys) or N$^\alpha$N$^\gamma$, N$^\delta$-triadamantyloxycarbonyl-L-arginine (hereinafter tri-Adoc-L-arginine) for pyro-L-glutamic acid and by following substantially the procedure of Example 13, the corresponding bis-boc-L-Lys or tri-Adoc-L-Arg derivatives of L-Phe-benzyl ester will be synthesized. Bis-boc-L-Lys is commercially available. Tri-Adoc-L-Arg is prepared according to Jäger, G. and Geiger, R., *Chem. Ber.* 103, 1727 (1970).

By substituting the benzyl esters of Gly, Ala, Trp, Tyr, Ile, Leu, His or Val, in the procedures of Examples 13 and 16, the corresponding pyro-L-glutamyl, bis-boc-L-Lys and tri-Adoc-L-Arg derivatives are obtained. The foregoing benzyl esters are commercially available. Benzyl ester protecting groups are removed essentially as described in Example 14.

EXAMPLE 17

The compounds resulting from Example 16 are reacted with any of the compounds resulting from the procedures of Examples 4–12, following essentially the procedures of Example 15, to yield the corresponding bis-boc-L-Lys and tri-Adoc-L-Arg derivatives. The bis-boc and tri-Adoc protecting groups are removed by treatment with trifluoroacetic acid in anisole.

Following essentially the procedures and methods of Examples 2–17, a family of thiolester compounds is obtained which have the general formula

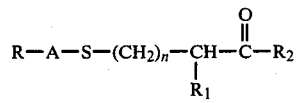

wherein,

R is L-arginyl, L-lysyl or L-pyroglutamyl;
A is L-phenylalanyl, glycyl, L-alanyl, L-tryptophyl, L-tyrosyl, L-isoleucyl, L-leucyl, L-histidyl, or L-valyl;
R$_1$ is hydrogen or methyl;
R$_2$ is L-proline, L-3,4-dehydroproline, D,L-3,4-dehydroproline, L-3-hydroxyproline, L-4-hydroxyproline or L-thiazolidine-4-carboxylic acid whose imino group is in imide linkage with the

and n is 0 or 1 such as when n=0, R$_1$ is methyl.

EXAMPLE 18

Oral effectiveness of N$^\alpha$-[3-(pyro-L-glutamyl-L-phenylalanylthio)-2-D-methyl-propanoyl]-L-proline Rats (210–290 g body weight) were fasted overnight and then anesthetized with intraperitoneal pentobarbital, 50–60 mg/kg. Tracheostomy was performed and the animals were ventilated mechanically. A cannula was inserted into a femoral vein for injection of angiotensin I, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 400 ng/ml of angiotensin I in 20 µl of 0.9 g % NaCl; an amount of angiotensin I sufficient to raise mean arterial blood pressure by 38 mm Hg. After the responsiveness of a given rat to angiotensin I was established, the named compound at 20 µmol/kg (drug dissolved in 0.15 ml of H$_2$O plus 10 µl of 1 N NaHCO$_3$), was given via a stomach tube. At timed intervals, the effects of 400 ng/kg of angiotensin I on mean arterial blood pressure were tested. Results are shown below:

| Time After Oral Administration (Minutes) | Blood Pressure Response to 400 ng/kg of Angiotensin I (% of Control) |
|---|---|
| −5 | 100 (38 mm Hg) |
| +1 | 53 |
| 5 | 66 |
| 15 | 26 |
| 18 | 26 |
| 21 | 21 |
| 25 | 21 |
| 29 | 24 |
| 39 | 18 |
| 44 | 16 |
| 49 | 16 |
| 54 | 18 |
| 60 | 18 |
| 74 | 18 |
| 86 | 21 |
| 110 | 21 |
| 120 | 26 |
| 132 | 26 |
| 142 | 26 |

EXAMPLE 19

Intravenous effectiveness of N$^\alpha$-[3-(pyro-L-glutamyl-L-phenylalanylthio)-2-D-methyl-propanoyl]-L-proline Anesthetized rats were prepared as described in Example 18. After the control reponse to 400 ng/kg angiotensin I was measured for a given rat, the named compound was administered via a femoral vein. The dose was 2 µmol/kg of the named compound in 15 µl 0.01 N sodium bicarbonate. The results are shown as percent of the control response.

| Time after intravenous administration (minutes) | Blood pressure response to 400 ng/kg angiotensin I (% of control) |
|---|---|
| −5 | 100% (38 mm Hg) |
| +½ (30 sec.) | 8 |
| 5 | 18 |
| 11 | 21 |
| 14 | 24 |
| 17 | 29 |
| 20 | 34 |
| 24 | 42 |
| 32 | 47 |
| 43 | 53 |
| 49 | 58 |
| 56 | 61 |
| 71 | 71 |
| 76 | 68 |
| 88 | 76 |
| 99 | 76 |
| 109 | 74 |
| 125 | 84 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A new compound having the formula

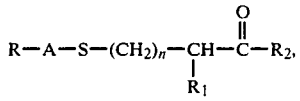

wherein

R is L-arginyl, L-lysyl or L-pyroglutamyl;

A is L-phenylalanyl, glycyl, L-alanyl, L-tryptophyl, L-tyrosyl, L-isoleucyl, L-leucyl, L-histidyl, or L-valyl whose amino group is in amide linkage with R;

$R_1$ is hydrogen or methyl;

$R_2$ is a residue of L-proline, L-3,4-dehydroproline, D,L-3,4-dehydroproline, L-3-hydroxyproline, L-4-hydroxyproline or L-thiazolidine-4-carboxylic acid whose imino group is in imide linkage with the adjacent

and, n is 0 or 1, such that when n=0, $R_1$ is methyl.

2. A compound of claim 1 wherein $R_2$ is L-proline.

3. A compound of claim 1 wherein $R_2$ is L-3,4-dehydroproline.

4. A compound of claim 1, 2 or 3 wherein R is L-pyroglutamyl, A is L-phenylalanyl, n is 1 and $R_1$ is methyl.

5. A compound of claim 1, 2 or 3 wherein A is L-phenylalanyl, L-tryptophyl, L-tyrosyl or L-histidyl.

6. A compound of claim 1, 2 or 3 wherein A is glycyl, L-alanyl, L-isoleucyl, L-leucyl or L-valyl.

7. A method for inhibiting angiotensin converting enzyme in vivo comprising administering an effective dose of a compound having the formula

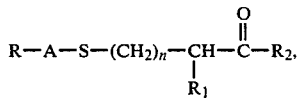

wherein

R is L-arginyl, L-lysyl or L-pyroglutamyl;

A is L-phenylalanyl, glycyl, L-alanyl, L-tryptophyl, L-tyrosyl, L-isoleucyl, L-leucyl, L-histidyl, or L-valyl whose amino group is in amide linkage with R;

$R_1$ is hydrogen or methyl:

$R_2$ is a residue of L-proline, L-3,4-dehydroproline, D,L-3,4-dehydroproline, L-3-hydroxyproline, L-4-hydroxyproline or L-thiazolidine4-carboxylic acid whose imino group is in imide linkage with the adjacent

and, n is 0 or 1, such that when n=0, $R_1$ is methyl.

8. The method of claim 7 wherein $R_2$ is L-proline.

9. The method of claim 7 wherein $R_2$ is L-3,4-dehydroproline.

10. The method of claim 7, 8 or 9 wherein R is L-pyroglutamyl, A is L-phenylalanyl, n is 1 and $R_1$ is methyl.

11. The method of claim 7, 8 or 9 wherein A is L-phenylalanyl, L-tryptophyl, L-tyrosyl or L-histidyl.

12. The method of claim 7, 8 or 9 wherein A is glycyl, L-alanyl, L-isoleucyl, L-leucyl, or L-valyl.

13. A method for reducing blood pressure in vivo comprising administering an effective dose of a compound having the formula R—A—S—(CH$_2$)$_n$—CH(R$_1$)—C(=O)—R$_2$, wherein R is L-arginyl, L-lysyl or L-pyroglutamyl;

A is L-phenylalanyl, glycyl, L-alanyl, L-tryptophyl, L-tyrosyl, L-isoleucyl, L-leucyl, L-histidyl, or L-valyl whose amino group is in amide linkage with R;

$R_1$ is hydrogen or methyl;

$R_2$ is a residue of L-proline, L-3,4-dehydroproline, D,L-3,4-dehydroproline, L-3-hydroxyproline, L-4-hydroxyproline or L-thiazolidine-4-carboxylic acid whose imino group is in imide linkage with the adjacent

—C(=O)—;

and, n is 0 or, such that when n=0, $R_1$ is methyl.

14. The method of claim 13 wherein $R_2$ is L-proline.

15. The method of claim 13 wherein $R_2$ is L-3,4-dehydroproline.

16. The method of claim 13, 14 or 15 wherein R is L-pyroglutamyl, A is L-phenylalanyl, n is 1 and $R_1$ is methyl.

17. The method of claim 13, 14 or 15 wherein A is L-phenylalanyl, L-tryptophyl, L-tyrosyl or L-histidyl.

18. The method of claim 13, 14 or 15 wherein A is glycyl, L-alanyl, L-isoleucyl, L-leucyl or L-valyl.

* * * * *

UNITED STATES PATENT AND TRADEMARK OFFICE
CERTIFICATE OF CORRECTION

PATENT NO. : 4,698,355
DATED : October 6, 1987
INVENTOR(S) : James W. Ryan and Alfred Chung It is certified that error appears in the above-identified patent and that said Letters Patent is hereby corrected as shown below:

Col. 4, line 7, delete the "be" before "reference" and add "by" in its place so that it reads "by reference"

Col. 9, line 18, "Trademark" should read "[1]Trademark"

Col. 9, line 24, delete "arginine" from the expression "(tri-Adoc-L-arginine)" and add the abbreviation "Arg" in its place so that it reads "(tri-Adoc-L-Arg)"

Col 12, line,. add "-" after "L-thiazolidine" and before "4" so that it reads "L-thiazolidine-4"

Signed and Sealed this

Fourth Day of October, 1988

Attest:

DONALD J. QUIGG

Attesting Officer

Commissioner of Patents and Trademarks